(12) United States Patent
Murphy et al.

(10) Patent No.: US 7,737,307 B2
(45) Date of Patent: Jun. 15, 2010

(54) FLUORINATED NONIONIC SURFACTANTS

(75) Inventors: Peter Michael Murphy, Chadds Ford, PA (US); Andrew Edward Feiring, Wilmington, DE (US); Stephan James McLain, Wilmington, DE (US); Jessica Sinks, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 326 days.

(21) Appl. No.: 11/890,375

(22) Filed: Aug. 6, 2007

(65) Prior Publication Data

US 2009/0043133 A1 Feb. 12, 2009

(51) Int. Cl.
*C07C 43/11* (2006.01)

(52) U.S. Cl. .................. 568/615; 106/14.05; 514/723; 252/79.1; 510/506

(58) Field of Classification Search .................. None
See application file for complete search history.

(56) References Cited

U.S. PATENT DOCUMENTS

| | | | |
|---|---|---|---|
| 6,512,058 B1 | 1/2003 | Haubennestel et al. |
| 6,989,035 B2 | 1/2006 | Scheper et al. |
| 7,144,431 B2 | 12/2006 | Gardner et al. |
| 2005/0107645 A1 | 5/2005 | Furukawa |
| 2005/0127322 A1 | 6/2005 | Costello et al. |
| 2005/0189299 A1 | 9/2005 | Malvasi et al. |
| 2007/0004938 A1 | 1/2007 | Guerra |

FOREIGN PATENT DOCUMENTS

| | | |
|---|---|---|
| GB | 1108128 | 4/1968 |
| GB | 1377766 A | 12/1974 |
| JP | 2005215153 A | 8/2005 |
| JP | 2006049037 A | 2/2006 |
| JP | 2006169503 A | 6/2006 |
| RU | 2263694 | 11/2005 |
| WO | WO 90/02110 | 3/1990 |
| WO | WO 2005/084191 A2 | 9/2005 |

OTHER PUBLICATIONS

Chi et al., A Facile Synthesis of Partly-fluorinated Ethers Using Perfluoropropoxyethylene and Aliphatic Alcohols, Bull. Korean Chem. Soc. (1999), vol. 20, No. 2, 220-222.

*Primary Examiner*—Rosalynd Keys
(74) *Attorney, Agent, or Firm*—Nancy S. Mayer

(57) ABSTRACT

A compound comprising Formula I, or a mixture thereof, $$R_f\text{—OCFHCF}_2\text{O—}[CH_2CH_2O]_x\text{—}[C_3H_7O]_y\text{-A} \quad \text{Formula I}$$

wherein
$R_f$ is $C_nF_{2n+1}$,
n is 1 to about 6,
x is a mixture of positive integers and is 4 or greater,
y is 0 to about 4, provided that the ratio of y to x is equal to or less than 0.25,
A is $R_fOCHFCF_2$ or $C_mH_{2m+1}$, and
m is 1 to about 24
and its use in lowering surface tension and imparting improved surface effects is disclosed.

16 Claims, No Drawings

FLUORINATED NONIONIC SURFACTANTS

FIELD OF THE INVENTION

The present invention relates to compositions comprising fluorinated nonionic surfactants useful for lowering surface tension and imparting improved surface effects.

BACKGROUND OF THE INVENTION

Most commercially available fluorinated surfactants are produced through electrochemical fluorination, telomerization, and oligomerization. Electrochemical fluorination utilizes anhydrous hydrofluoric acid as the fluorine source. However, industrially produced hydrofluoric acid contains impurities, which requires further complicated methods to remove these impurities.

Telomerization or oligomerization processes use tetrafluoroethylene as the starting material. However, the source of available tetrafluoroethylene is limited. The product obtained from a telomerization process usually contains a mixture of homologs having different carbon chain lengths resulting in telomers with a distribution of carbon chain lengths. Therefore, the sequential separation of telomerization products is required in order to produce fluorosurfactants which contain a fixed length of the fluorinated carbon chain, as described by Erik Kissa in "Fluorinated Surfactants, Synthesis-Properties-Applications" Surfactant Science Series, Vol. 50, Marcel Dekker, New York, (1994).

U.S. Patent Application 20050127322 describes a hydrofluoroether heat transfer fluid which is represented by the following structure: $R_f$—O—$R_h$—O $R_f'$ wherein $R_h$ is independently an alkylene group having from 2 to about 8 carbon atoms and at least 4 hydrogen atoms. The syntheses described in the examples of above patent application show these materials to be water insoluble; therefore, they are not suitable as surfactants.

It is desirable to have a composition comprising fluorinated surfactants which can be produced from starting materials other than tetrafluoroethylene. It is also desirable to have a method of lower surface tension using a very low concentration of surfactant, and to provide surface effects. The present invention provides such a composition comprising fluorinated nonionic surfactants which are produced from reacting fluoroalkyl vinyl ether with polyethylene glycol. The present invention also provides methods of providing surface effects to various liquids

SUMMARY OF THE INVENTION

The present invention comprises a compound comprising Formula I, or a mixture thereof, $$R_f\text{—OCFHCF}_2\text{O—[CH}_2\text{CH}_2\text{O]}_x\text{—[C}_3\text{H}_7\text{O]}_y\text{-A} \qquad \text{Formula I}$$

wherein
$R_f$ is $C_nF_{2n+1}$,
n is 1 to about 6,
x is a mixture of positive integers and is 4 or greater,
y is 0 to about 4, provided that the ratio of y to x is equal to or less than 0.25,
A is $R_f\text{OCHFCF}_2$ or $C_mH_{2m+1}$, and
m is 0 to about 24.

The present invention further comprises a method of altering the surface behavior of a liquid comprising adding to the liquid a compound of Formula I as described above.

The present invention further comprises a method of lowering the surface tension of a liquid comprising adding to the liquid a compound of Formula I as described above.

DETAILED DESCRIPTION OF THE INVENTION

All trademarks are denoted herein by capitalization. All patents and patent applications cited herein are hereby incorporated by reference.

The present invention comprises a compound comprising Formula I, or a mixture thereof, $$R_f\text{—OCFHCF}_2\text{O—[CH}_2\text{CH}_2\text{O]}_x\text{—[C}_3\text{H}_7\text{O]}_y\text{-A} \qquad \text{Formula I}$$

wherein
$R_f$ is $C_nF_{2n+1}$,
n is 1 to about 6,
x is a mixture of positive integers and is 4 or greater,
y is 0 to about 4, provided that the ratio of y to x is equal to or less than 0.25,
A is $R_f\text{—OCHFCF}_2$ or $C_mH_{2m+1}$, and
m is 0 to about 24.

In the Formula I, $R_f$ is a straight or branched perfluoroalkyl group having from 1 to about 6 carbon atoms, preferably having from 1 to about 4 carbon atoms. In Formula I, x is a positive integer, or a mixture thereof, equal to or greater than about 4. Preferably x is a mixture of from about 4 to about 45, more preferably a mixture of from about 9 to about 25. Preferably m is 0 to about 12, more preferably m is 0.

A preferred embodiment of Formula 1 is that wherein $R_f$ is $C_3F_7$, x is from about 12 to about 18, y is 0, and A is $R_f\text{—OCHFCF}_2$. An additional preferred embodiment of Formula 1 is that wherein $R_f$ is $C_3F_7$, x is from about 12 to about 18, y is 0, and A is $C_mH_{2m+1}$, wherein m is 0.

The compound of Formula I is a fluorinated nonionic surfactant which lowers surface tension using a very low concentration of the surfactant of less than about 5%, preferably less than about 1%, more preferably less than about 0.1%. The compound of Formula I can be used to obtain surface tension of less than about 25 mN/M, preferably less than about 20 mN/M, at a concentration of about 0.1% by weight in water. The surfactant is characterized by its efficiency in lowering the surface tension at low concentrations by selective adsorption on the interface, which is determined by the amphiphilic nature of the surfactant. The term "amphiphilic" means attraction to two different kinds of media. The surfactants comprise a water-soluble hydrophilic part and a water-insoluble hydrophobic part.

The compound of the present invention of Formula I comprises at least one hydrophobic part which contains the $R_f$ perfluoroalkyl group. The compound of the present invention of Formula I further comprises one hydrophobic portion represented by moiety A which is either an $R_f$ perfluoroalkyl group, or a unfluorinated alkyl group represented by $C_mH_{2m+1}$ wherein m is from 1 to about 24. As a result, the compound of Formula I of the present invention is able to lower surface tension at very low concentration. Having one or both of the hydrophobic parts as $R_f$ perfluoroalkyl group(s), the compound of Formula I of the present invention exhibits various levels of hydrophobic and oleophobic properties. Therefore Formula I is suitable for providing improved surface effects including blocking resistance, enhanced hiding power (leveling), spreading, wettability, penetrability, foam inhibition and dispersibility. The improved surface effects by the compounds of the present invention are suitable for many industrial applications including aqueous coatings such as inks, paints, varnishes, and the like.

The compound of Formula I also comprises a hydrophilic portion which contains a polyethylene glycol having at least 10 carbon atoms. When the moiety A is $C_mH_{2m+1}$ and m is 0, the hydroxyl end group also serves as a hydrophilic group. The hydrophilic part provides effective hydrosolubility in water media, and therefore the compound represented by Formula I of the present invention exhibits surfactant properties. The hydrophilic part of the compound of Formula I optionally contains polypropylene glycol. The compound of Formula I is a nonionic fluorinated surfactant.

The compounds of Formula I are prepared by reacting a fluorinated vinyl ether with a polyethylene glycol. Typically the vinyl ether is slowly added to the glycol in a molar ratio of from about 1:1 to about 3:1, preferably at about 2:1. The reaction is conducted in the presence of NaH which is a catalyst that is basic enough to generate equilibrium amounts of the alkoxide anion from the glycol. Other suitable base catalysts include KH, sodium amide, lithium amide, potassium tert-butoxide, and KOH. The reaction is conducted under an inert atmosphere such as nitrogen gas. Suitable solvents include dimethylformamide, dimethylacetamide, acetonitrile, tetrahydrofuran, and dioxane. Preferred is dimethylformamide. Cooling is employed to maintain the reaction temperature at from about 0° C. to about 30° C. The reaction is usually conducted for 1 to about 18 hours. The solvent is then removed using conventional techniques; such as evaporation in vacuo on a rotary evaporator, or in cases where the product is water insoluble and the solvent is water soluble, addition of the mixture to an excess of water followed by separation of the layers.

The reaction of perfluoropropyl vinyl ether with polyethylene glycol does not always go to completion. The average degree of conversion of the polyethylene glycol hydroxyl groups can be determined by $^1$H NMR spectroscopy. Typically mixtures of unreacted polyethylene glycol, the product of fluorinated vinyl ether adding to one end of polyethylene glycol (for example, structure B below), and the product of fluorinated vinyl ether adding to both ends of the polyethylene glycol (for example, structure A below) can be obtained. The relative amounts of the components of the mixture are affected by the ratio of the reactants, the reaction conditions, and the way in which the product is isolated. High ratios of the vinyl ether to glycol and long reaction times tend to favor Structure A, shown below. Lower ratios of vinyl ether to glycol and shorter reaction times give increased amounts of Structure B, shown below, and unreacted polyethylene glycol. As illustrated in the Examples herein it is sometimes possible to use the differences in solubility between Structures A, B, and the starting glycol to do selective solvent extraction of mixtures to obtain samples that are highly enriched in Structures A or B. In some cases the mixture contains predominately Structure A. In other cases the mixture contains predominately Structure B based on the average degree of conversion determined by $^1$H NMR, and by the method of workup.

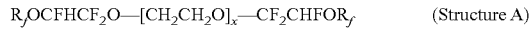

R$_f$OCFHCF$_2$O—[CH$_2$CH$_2$O]$_x$—CF$_2$CHFOR$_f$  (Structure A)

R$_f$OCFHCF$_2$O—[CH$_2$CH$_2$O]$_x$H  (Structure B)

Suitable polyethylene glycols for use in the present invention contain either an individual oligomer of polyethylene glycol, or a mixture of a distribution of individual oligomers of polyethylene glycols, which contain at least about 10 carbon atoms (x in Formula I is at least about 4) and have an average molecular weight of between about 200 and about 3000. Preferably the polyethylene glycol contains from about 10 carbon atoms to about 90 carbon atoms (x in Formula I is from about 5 to about 45) and has an average molecular weight of between about 200 and about 2000. More preferably, the polyethylene glycol contains from about 10 carbon atoms to about 60 carbon atoms (x in Formula I is from about 5 to about 30) and has an average molecular weight of from about 200 to about 1500. Polyethylene glycols suitable for the use in the present invention as described above are commercially available from Sigma-Aldrich, Milwaukee, Wis.

The fluorinated vinyl ether used in the above reaction is made by various methods. These methods include making fluorinated vinyl ethers by reacting a 2-alkoxypropionyl fluoride in a stationary bed of a metal carbonate, a tubular reactor filled with dried metal carbonate and equipped with a screw blade running through the tube, or a fluidized bed of metal carbonate. U.S. Patent Application 2007/0004938 describes a process to produce fluorinated vinyl ether by reacting a 2-alkoxypropionyl fluoride with a metal carbonate under anhydrous conditions in a stirred bed reactor at a temperature above the decarboxylation temperature of an intermediate carboxylate to produce fluorinated vinyl ether. Examples of fluorinated vinyl ethers suitable for use in the present invention include CF$_3$—O—CF=CF$_2$, CF$_3$CF$_2$—O—CF=CF$_2$, CF$_3$CF$_2$CF$_2$—O—CF=CF$_2$, and CF$_3$CF$_2$CF$_2$CF$_2$—O—CF=CF$_2$, each of which are available from E.I. du Pont de Nemours and Company, Wilmington, Del.

The present invention further comprises a method of lowering surface tension of a liquid comprising adding to the liquid a compound of Formula I as described above. The surfactants of Formula I of the present invention are effective in lowering the surface tension of a wide variety of media. Examples of suitable medium include, for example, a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent. Adding a composition of the present invention to the medium results in lowering the surface tension of the medium due to the surfactant properties of the composition of the present invention. The composition of the present invention is typically simply blended with or added to the medium. These surfactants are especially suitable for lowering the surface tension of water, aqueous solutions, and aqueous emulsions. A low concentration of less than about 0.1%, preferably less than about 0.01% by weight of a compound of Formula I in the liquid is effective.

The present invention further comprises a method of altering the surface behavior of a liquid comprising adding to the liquid a compound of Formula I as defined above. A wide variety of surface behaviors is included. Examples are wetting, penetration, spreading, leveling, flowing emulsification, stabilizing and dispersion in the wet liquids. Other examples include antiblocking, repellency and releasing in a dried coating composition on a treated substrate. Consequently, the surfactants of Formula I are useful in a wide variety of end use applications.

The compound of Formula I of the present invention is suitable for use in coatings, paints, pigments, varnishes, finishing agents, floor waxes, inks and dyes. Surface effects provided include enhanced hiding power, leveling, antiblocking and anticratering, control of soiling, water and oil repellency, wetting, dispersion, blocking resistance, color development, and to combat pigment flotation problems.

Particular coating compositions suitable for use with the surfactants of the present invention, referred to herein by the term "coating base", include a composition, typically a liquid formulation, of an alkyd coating, Type I urethane coating, unsaturated polyester coating, or water-dispersed coating, and is applied to a substrate for the purpose of creating a lasting film on the substrate surface. These are conventional paints, stains, and similar coating compositions.

By the term "alkyd coating" as used herein is meant a conventional liquid coating based on alkyd resins, typically a paint, clear coating, or stain. The alkyd resins are complex branched and cross-linked polyesters containing unsaturated aliphatic acid residues. Conventional alkyd coatings utilize, as the binder or film-forming component, a curing or drying alkyd resin. Alkyd resin coatings contain unsaturated aliphatic acid residues derived from drying oils. These resins spontaneously polymerize in the presence of oxygen or air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the unoxidized alkyd resin or drying oil. Such drying oils have been used as raw materials for oil-based coatings and are described in the literature.

By the term "urethane coating" as used hereinafter is meant a conventional liquid coating based on Type I urethane resins, typically a paint, clear coating, or stain. Urethane coatings typically contain the reaction product of a polyisocyanate, usually toluene diisocyanate, and a polyhydric alcohol ester of drying oil acids. Urethane coatings are classified by ASTM D-1 into five categories. Type I urethane coatings contain a pre-reacted autoxidizable binder as described in Surface Coatings Vol. I, previously cited. These are also known as uralkyds, urethane-modified alkyds, oil-modified urethanes, urethane oils, or urethane alkyds, are the largest volume category of polyurethane coatings and include paints, clear coatings, or stains. The cured coating is formed by air oxidation and polymerization of the unsaturated drying oil residue in the binder.

By the term "unsaturated polyester coating" as used hereinafter is meant a conventional liquid coating based on unsaturated polyester resins, dissolved in monomers and containing initiators and catalysts as needed, typically as a paint, clear coating, or gel coat formulation. Unsaturated polyester resins contain as the unsaturated prepolymer the product obtained from the condensation polymerization of a glycol such as 1,2-propylene glycol or 1,3-butylene glycol with an unsaturated acid such as maleic (or of maleic and a saturated acid, e.g., phthalic) in the anhydride form. The unsaturated prepolymer is a linear polymer containing unsaturation in the chain. This is dissolved in a suitable monomer, for instance styrene, to produce the final resin. The film is produced by copolymerization of the linear polymer and monomer by means of a free radical mechanism. The free radicals can be generated by heat, or more usually by addition of a peroxide, such as benzoyl peroxide, separately packaged and added before use. Such coating compositions are frequently termed "gel coat" finishes. For curing coatings at room temperature, the decomposition of peroxides into free radicals is catalyzed by certain metal ions, usually cobalt. The solutions of peroxide and cobalt compound are added separately to the mix and well stirred before application. The unsaturated polyester resins that cure by a free radical mechanism are also suited to irradiation curing using, for instance, ultraviolet light. This form of cure, in which no heat is produced, is particularly suited to films on wood or board. Other radiation sources, for instance electron-beam curing, are also used.

By the term "water-dispersed coatings" as used herein is meant coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as well as members of other classifications. Water-dispersed coatings in general contain other common coating ingredients. Water-dispersed coatings are exemplified by, but not limited to, pigmented coatings such as latex paints, unpigmented coatings such as wood sealers, stains, and finishes, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

By the term "dried coating" as used herein is meant the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

Blocking is the undesirable sticking together of two coated surfaces when pressed together, or placed in contact with each other for an extended period of time. When blocking occurs separation of the surfaces can result in disruption of the coating on one or both surfaces. Thus improved resistance to blocking is beneficial in many situations where two coated surfaces need to be in contact, for example on window frames.

When used as additives to a coating base the compositions of the present invention of Formula I as defined above are effectively introduced to the coating base or other composition by thoroughly stirring it in at room or ambient temperature. More elaborate mixing can be employed such as using a mechanical shaker or providing heat or other methods. Such methods are not necessary and do not substantially improve the final composition. When used as an additive to latex paints, the compositions of the invention generally are added at about 0.001 weight % to about 5 weight % by dry weight of the composition of the invention in the wet paint. Preferably about from about 0.01 weight % to about 1 weight %, and more preferably from about 0.1 weight % to about 0.5 weight % is used.

Floor waxes, polishes, or finishes (hereinafter "floor finishes") are generally water based or solvent based polymer emulsions. The surfactants of Formula I of the present invention are suitable for use in such floor finishes. Commercially available floor finish compositions typically are aqueous emulsion-based polymer compositions comprising one or more organic solvents, plasticizers, coating aides, anti-foaming agents, surfactants, polymer emulsions, metal complexing agents, and waxes. The particle size range and solids content of the polymer are usually controlled to control the product viscosity, film hardness and resistance to deterioration. Polymers containing polar groups function to enhance solubility and may also act as wetting or leveling agents providing good optical properties such a high gloss and distinctness of reflected image.

Preferred polymers for use in floor finishes include acrylic polymers, polymers derived from cyclic ethers, and polymers derived from vinyl substituted aromatics. Acrylic polymers include various poly(alkyl acrylates), poly(alkyl methacrylates), hydroxyl substituted poly(alkyl acrylates) and poly (alkyl methacrylates). Commercially available acrylic copolymers used in floor finishes include, for example, methyl methacrylate/butyl acrylate/methacrylic acid (MMA/ BA/MM) copolymers; methyl methacrylate/butyl acrylate/ acrylic acid (MMA/BA/A) copolymers, and the like. Commercially available styrene-acrylic copolymers include styrene/methyl methacrylate/butyl acrylate/methacrylic acid (S/MMA/BA/MMA) copolymers; styrene/methyl methacrylate/butyl acrylate/acrylic acid (S/MMA/BA/AA) copolymers; and the like. Polymers derived from cyclic ethers usually contain 2 to 5 carbon atoms in the ring with optional alkyl groups substituted thereon. Examples include various oxiranes, oxetanes, tetrahydrofurans, tetrahydropyrans, dioxanes, trioxanes, and caprolactone. Polymers derived from vinyl substituted aromatics include for example those made from styrenes, pyridines, conjugated dienes, and copolymers thereof. Polyesters, polyamides, polyurethanes and polysiloxanes are also used in floor finishes.

The waxes or mixtures of waxes that are used in floor finishes include waxes of a vegetable, animal, synthetic, and/ or mineral origin. Representative waxes include, for example, carnuba, candelilla, lanolin, stearin, beeswax, oxidized polyethylene wax, polyethylene emulsions, polypropylene, copolymers of ethylene and acrylic esters, hydrogenerated coconut oil or soybean oil, and the mineral waxes such as paraffin or ceresin. The waxes typically range from 0 to about 15 weight percent and preferably from about 2 to about 10 weight percent based on the weight of the finish composition.

When used as additives to a floor finish the compositions of the present invention of Formula (I) as defined above are effectively introduced to the composition by thoroughly stirring it in at room or ambient temperature. More elaborate mixing can be employed such as using a mechanical shaker or providing heat or other methods. When used as an additive to floor finishes, the compositions of the invention generally are added at about 0.001 weight % to about 5 weight % by dry weight of the composition of the invention in the wet composition. Preferably about from about 0.01 weight % to about 1 weight %, and more preferably from about 0.1 weight % to about 0.5 weight % is used.

Floor waxes or polishes are water based, solvent based and polymer. The surfactants of the present invention are suitable for use with any of these. Water-based and polymer waxes dry to a high gloss without buffing; solvent-based wax requires vigorous buffing. Water-based wax is recommended for asphalt, vinyl, vinyl asbestos and rubber-tiled floors; solvent-based waxes produce a hard, shiny finish and are best for wood, cork and terrazzo floors. Self-polishing waxes, such as polymer or resin, will yellow or discolor and wear off in heavy traffic areas; they should be stripped off and reapplied after three or four coats.

The compounds of Formula I are useful in many additional applications. Examples of some applications include the following.

The compounds represented by Formula I of the present invention are suitable for the use in fire fighting compositions, for example as a wetting agent, emulsifying agent and/or dispersion. They are also useful as a component in aqueous film forming extinguishing agents, and as an additive to dry chemical extinguishing agents in aerosol-type extinguishers, and as a wetting agent for sprinkler water.

The compounds of Formula I of the present invention are suitable for the use in agricultural compositions. Examples include as a wetting agent, emulsifying agent and/or dispersion agent for herbicides, fungicides, weed killers, parasiticides, insecticides, germicides, bactericides, nematocides, microbiocides, defolients, fertilizers and hormone growth regulators. Formula I compounds are also suitable as a wetting agent for foliage, for live stock dips and to wet live stock skins; as an ingredient in sanitizing, discoloring and cleaning compositions; and in insect repellent compositions. The compounds of Formula 1 are also useful as a wetting agent, emulsifying agent and/or dispersion agent for the manufacture of paper and plywood veneer. The compounds of Formula I are also suitable for use as grease/oil repellents for paper, wood, leather, skins, metals, textiles, stone, and tiles, and as penetrant for preservative impregnation.

The compounds represented by Formula I of the present invention are also suitable for the use as a wetting agent, emulsifying agent and/or dispersion agent for polymerization reactions, particularly polymerization of fluoromonomers. These compounds are also suitable as a latex stabilizer; as an additive for foam applications to control spreading, crawling and edge buildup; as foaming agents, as mold release agents or as demolding agents; as an internal antistatic agent and antiblocking agent for polyolefins; as a flow modifier for extruding hot melts, spreading, uniformity, anticratering; and as a retarder for plasticizer migration or evaporation in the plastics and rubber industry.

The compounds of Formula I of the present invention are further suitable for the use in the petroleum industry as a wetting agent for oil well treatments, drilling mud; as a film evaporation inhibitor for gasoline, jet fuel, solvents, and hydrocarbons; as a lubricant or cutting oil improver to improve penetration times; as an oil spill collecting agent; and as additive to improve tertiary oil well recovery.

The compounds of Formula I of the present invention are further suitable for the use in textile and leather industries as a wetting agent, antifoaming agent, penetrating agent or emulsifying agent; or as a lubricant for textiles, nonwoven fabrics and leather treatment; for fiber finishes for spreading, and uniformity; as a wetting agent for dyeing; as a binder in nonwoven fabrics; and as a penetration additive for bleaches.

The compounds of Formula I of the present invention are further suitable for the use in the mining and metal working industries, in the pharmaceutical industry, automotives, building maintenance and cleaning, in household, cosmetic and personal products, and in photography and graphic arts to provide improved surface effects.

Test Methods

The following test methods are used in the Examples herein.

Test Method 1—Surface Tension

The surface tension of each sample was measured in accordance with the following procedure. An aliquot (30 mL) of each aqueous solution containing a sample to be tested was poured into separate glass dishes and allowed to equilibrate for 20-30 seconds before measurements were taken. The measurements were conducted using a Krüss K11 tensiometer (available from Krüss GmbH, Hamburg, Germany) using the 'Wilhelmy Plate Method' wherein a small platinum plate with a roughened surface was suspended perpendicular to the liquid surface contained in the glass dish. The plate was attached to a force measuring balance. The glass dish was raised manually until the surface of the liquid was a few millimeters in distance from the suspended plate. The dish was then raised electronically and the wetting of the plate provided for a force proportional to the surface tension of the liquid. A mean surface tension value was obtained from ten consecutive readings and reported in units of milli-newtons/meter (mN/M). A lower value indicates superior performance.

Test Method 2—Leveling Effect in Floor Finishes (Waxes)

To test the performance of samples in their wetting and leveling ability, the samples were added to a floor polish RHOPLEX 3829, Formulation N-29-1, which is available from Rohm and Haas Company, Philadelphia, Pa., and applied to half of a stripped 12 inch×12 inch (30.36 cm×30.36 cm) vinyl tile. A 1% (active ingredient basis) solution of the surfactant to be tested was prepared by dilution in deionized water. Following the resin manufacturer protocols, a 100 g portion of the RHOPLEX 3829 formulation was prepared, followed by addition of 0.75 g of the 1% (active ingredient basis) surfactant solution, to provide a test floor polish.

The test floor polish was applied to the tile by placing a 3 mL portion of the test polish in the center of the tile, and spreading from top to bottom using an applicator, and finally placing a large "X" across the tile, using the applicator. The tile was allowed to dry for 30 min and a total of 5 coats were applied. After each coat, the tile was rated on a 1 to 5 scale (1 being the worst, 5 the best) on the surfactant's ability to promote wetting and leveling of the polish on the tile surface. The rating is determined based on comparison of a tile treated with the floor polish that contained no fluorosurfactant with a higher rating indicating superior performance.

Subjective Tile Rating Scale

1 Uneven surface coverage of the film, significant streaking and surface defects 2 Visible streaking and surface defects, withdrawal of the film from the edges of the tile 3 Numerous surface defects and streaks are evident but, generally, film coats entire tile surface 4 Minor surface imperfections or streaking 5 No visible surface defects or streaks.

Test Method 3—Blocking Resistance in Semi-Gloss Latex Paint

The blocking resistance of paints was measured according to a slightly amended version of an ASTM method (D 4946-89). This test method describes an accelerated procedure for evaluating the face-to-face blocking resistance of commercial architectural paints and the paints which contained the compound of the Formula I of the present invention. Blocking, for the purpose of this test, is defined as the undesirable sticking together of two painted surfaces when pressed together or placed in contact with each other for an extended period of time. The paint to be tested was cast on a polyester test panel using an applicator blade. The coated panels were conditioned in a room which was maintained at 18 to 29° C. and 40-60% relative humidity for 24 hours. After the panels were conditioned for 24 hours, six squares (3.8 cm square) were cut from the painted test panel. The cut sections (three pairs) were positioned with the painted surfaces face-to-face for each of the paints to be tested, and a pressure of about 1.8 psi (127 g/cm2) was applied. The paint films were placed in an oven for 30 minutes at 50° C. to increase the severity of the test. After cooling, the panels were peeled apart. The degree of blocking was measured on a subjective scale for tack or seal, using a series of descriptive terms corresponding to numerical ASTM values from 0 to 10. The rating system is described in the Table 1. The degree of seal was estimated from the appearance of the specimens; the fraction of the paint surfaces that adhered, or where paint tore away from the test panel backing was an indication of seal.

TABLE 1

| Blocking Resistance Numerical Ratings | Description of the Separation | Performance Description |
| --- | --- | --- |
| 10 | no tack | perfect |
| 9 | trace tack | excellent |
| 8 | very slight tack | very good |
| 7 | slight tack | good/very good |
| 6 | moderate to slight tack | good |
| 5 | moderate tack | fair |
| 4 | very tacky - no seal | poor to fair |
| 3 | 5 to 25% seal | poor |
| 2 | 25 to 50% seal | poor |
| 1 | 50 to 75% seal | very poor |
| 0 | 75 to 100% seal | very poor |

Test Method 4—Hiding Power (Leveling) in Semi-Gloss Latex Paint

The hiding power (leveling) of paints was measured according to a slightly amended version of the standard method, ASTM D2805-96a. This test method describes a procedure for evaluating the Hiding Power of architectural paint films via use of a Contrast Ratio, the photometric measure of the film opacity, or hiding. Hiding Power was defined as the Spreading Rate required for full hiding over a standard black and white substrate. The latter was defined in to have CIE-Y reflectances of 0.01 (1%) max. and 0.80 (80%) respectively. This method determined the Contrast Ratio using a specified film thickness for sample to sample comparison. Reflectometry measurement was performed using the Minolta Chroma Meter CR-200. The CIE color space (Y, y, x) was used, particularly the Y-tristimulus value. Polyester scrube test panels (Leneta "Opacity" or "Penopac" charts or the equivalent BYK-Gardner charts) were used.

The paint to be tested was evenly cast on the Opacity test chart using an applicator blade. 2 or 3 mil applicator blades can be used, but the film thickness must be equal for all samples tested. The photometric Contrast Ratio for the Control sample is less than 0.98, which was visually just short of total extinction of contrast. The coated charts were conditioned at room temperature for the desired period of time (no less than 40 hours). All painted charts were protected from surface contamination including grease, oil, fingerprints, dust, et cetera. The painted chart was placed on a level bench or platform. Using the reflectometer, the CIE tristimulus measurement mode was chosen. The Y-tristimulus value was measured and recorded in triplicate across different areas of the painted "black" portion of the chart. These values were averaged to obtain $R_0$ where $R_0$=reflectance over black substrate. The measuring and recording were repeated over the painted "white" portion of the chart. These values were averaged to obtain $R_{0.80}$ where $R_{0.80}$=reflectance over white substrate. $R_{0.80}$ is also referred to as $R_w$ in literature. The Contrast Ratio (C) was determined using the formula $C=R_0/R_{0.80}$. Contrast Ratios were graphically compared to one another for samples of the same wet film thickness. A higher Contrast Ratio indicates superior performance.

Materials

The following materials were used in the Examples herein:

Various polyethylene glycols used in the examples are characterized by the number average molecular weight ($M_n$) and by the average number of ethylene oxide (EO) repeating units as listed in Table 2A. Various polyethylene glycol monomethyl ethers used in the examples are characterized by the number average molecular weight ($M_n$) and by the average number of ethylene oxide (EO) repeating units as listed in Table 2B. These polyethylene glycols and ethers are available from Sigma-Aldrich, Milwaukee, Wis.

TABLE 2A

Polyethylene Glycols for Examples 1-10

| Example | Polyethylene Glycol $M_n$ (EO)* |
|---|---|
| 1 | 400 (8.7 EO) |
| 2 | 300 (6.4 EO) |
| 3 | 200 (4.1 EO) |
| 4 | 600 (13.2 EO) |
| 5 | 1000 (22 EO) |
| 6 | 1500 (34 EO) |
| 7 | 2000 (45 EO) |
| 8 | 400 (8.7 EO) |
| 9 | 600 (13.2 EO) |
| 10 | 1000 (22 EO) |

*EO = subscript x in Formula 1

TABLE 2B

Polyethylene Glycol mono-Methyl Ethers for Examples 11-14

| Example | Polyethylene Glycol mono-Methyl Ether $M_n$ (EO)* |
|---|---|
| 11 | 200 (4 EO) |
| 12 | 550 (12 EO) |
| 13 | 750 (17 EO) |
| 14 | 2000 (45 EO) |

*EO = subscript x in Formula 1

Perfluoropropyl vinyl ether available from E.I. du Pont de Nemours and Company, Wilmington, Del. was used in the preparation of the examples.

SOLKANE 365 mfc (1,1,1,3,3-pentafluorobutane) is available from Solvay Chemicals.

EXAMPLES

In the Examples the term "wt %" means percent by weight, and the abbreviation PPVE means perfluoropropylvinyl ether.

Example 1

In a dry box, a 250 mL 4 neck flask with a magnetic stir bar was charged with polyethylene glycol (40.0 g, 0.10 mole, Mn=400) and 80 mL of anhydrous DMF (Aldrich Sure/Seal™). NaH (0.48 g, 0.02 mole) was added slowly with stirring until the completion of hydrogen evolution. The flask was removed from the dry box, place under positive $N_2$ pressure, and an addition funnel containing perfluoropropylvinyl ether (PPVE, 63.8 g, 0.24 mole) was attached. The PPVE was added dropwise and an ice/water bath was used to remove heat from the exothermic reaction and maintain the temperature in the range of 0-30° C. At the end of the addition the mixture was stirred for an additional 2 h at room temperature. The entire reaction mixture was added to 400 mL water and this mixture was extracted with two 300 mL portions of ether in a separatory funnel. The combined ether extracts were washed with 300 mL water, dried over $MgSO_4$, and concentrated in vacuo on a rotary evaporator to give a light yellow oil (59.0 g). $^1$H NMR ($\delta$, $d_6$-benzene): 3.25, 3.33, 3.38, 3.44 (m, m, m, m, $CH_2$), 3.56 (m, $OCH_2\underline{CH}2OH$), 3.70 (t, $OCH_2C\underline{H}_2OCF_2CFHOC_3F_7$), 5.51 (t, $^3J_{H\text{-}F}=50$ Hz, $OCH_2CH_2OCF_2CF\underline{H}OC_3F_7$). Based on the integration of the unique peaks due to the PPVE end groups: 3.70 (2H) and 5.51 (1H) vs. the integration of all $CH_2$ peaks (34.8H), the conversion of hydroxyl groups is calculated to be 88%. Example 1 prepared above was dissolved in water at weight percent of 0.1%, and was tested for surface tension in accordance with Test Method 1. The results are in Table 3.

Example 2

Using the same procedure and workup as Example 3, polyethylene glycol (30.0 g, 0.10 mole, $M_n$=300), NaH (0.48 g, 0.02 mole), and perfluoropropylvinyl ether (PPVE, 63.8 g, 0.24 mole) were reacted to give 57.0 g product. Based on the integration of the $^1$H NMR spectrum the conversion of hydroxyl groups is calculated to be 84%. Example 2 prepared above was dissolved in water at weight percent of 0.1%, and was tested for surface tension in accordance with Test Method 1. The results are in Table 3.

Example 3

Using the same procedure and workup as Example 3, polyethylene glycol (20.0 g, 0.10 mole, $M_n$=200), NaH (0.48 g, 0.02 mole), and perfluoropropylvinyl ether (PPVE, 63.8 g, 0.24 mole) were reacted to give 57.0 g product. Based on the integration of the $^1$H NMR spectrum the conversion of hydroxyl groups is calculated to be 72%. Example 3 prepared above was dissolved in water at weight percent of 0.1%, and was tested for surface tension in accordance with Test Method 1. The results are in Table 3.

Example 4

In a dry box, a 500 mL Pyrex bottle was charged with polyethylene glycol (60.0 g, 0.10 mole, $M_n$=600) and 80 mL of anhydrous DMF (Aldrich Sure/Seal™). NaH (0.48 g, 0.02 mole) was added slowly with magnetic stirring until the completion of hydrogen evolution. The capped bottle was removed from the drybox, and the solution was transferred to a 400 mL metal shaker tube in a nitrogen filled glovebag. The shaker tube was cooled to an internal temperature of −18° C., shaking was started, and perfluoropropylvinyl ether (PPVE, 63.8 g 0.24 mole) was added from a metal cylinder. The mixture was allowed to warm to room temperature and was shaken for 20 h. The entire reaction mixture was added to 400 mL water and this mixture was extracted with two 300 mL portions of ether in a separatory funnel. The combined ether extracts were washed with 300 mL water, dried over $MgSO_4$, and concentrated in vacuo on a rotary evaporator to give a light yellow oil (91.0 g). $^1$H NMR ($\delta$, $d_6$-benzene): 3.25, 3.35, 3.40, 3.46 (m, m, m, m, $CH_2$), 3.70 (t, $OCH_2C\underline{H}_2OCF_2CFHOC_3F_7$), 5.52 (t, $^3J_{H\text{-}F}=53$ Hz, $OCH_2CH_2OCF_2CF\underline{H}OC_3F_7$). Based on the integration of the unique peaks due to the PPVE end groups: 3.70 (2H) and 5.52 (1H) vs. the integration of all $CH_2$ peaks (52.8H), the conversion of hydroxyl groups is 96%. This is consistent with the peak at 3.63 due to —$OCH_2C\underline{H}2OH$ being barely detectable.

$^{19}$F NMR (δ, d$_6$-acetone) −82.8 (CH$_2$OCF$_2$CHFOCF$_2$CF$_2$CF$_3$, 3F), −86.6 (AB q, CH$_2$OCF$_2$CHFOCF$_2$CF$_2$CF$_3$, 2F), −90.8 (CH$_2$OCF$_2$CHFOCF$_2$CF$_2$CF$_3$, 2F), −131.0 (CH$_2$OCF$_2$CHFOCF$_2$CF$_2$CF$_3$, 2F), −146.31 (CH$_2$OCF$_2$CHFOCF$_2$CF$_2$CF$_3$, 1F). Example 4 prepared above was dissolved in water at weight percent of 0.1%, and was tested for surface tension in accordance with Test Method 1. The results are in Table 3.

Example 5

In a dry box, a 250 mL 4 neck flask with a magnetic stir bar was charged with polyethylene glycol (30.0 g, 0.03 mole, M$_n$=1000) and 100 mL of anhydrous DMF (Aldrich Sure/Seal™). NaH (0.08 g, 0.003 mole) was added slowly with stirring until the completion of hydrogen evolution. The flask was removed from the dry box, place under positive N$_2$ pressure, and an addition funnel containing perfluoropropylvinyl ether (PPVE, 17.6 g, 0.066 mole) was attached. The PPVE was added dropwise and an ice/water bath was used to remove heat from the exothermic reaction and maintain the temperature in the range of 0-35° C. At the end of the addition the mixture was stirred for 18 hours at room temperature. The solvent and any volatile products were removed by Kugelrohr distillation under high vacuum at 140-150° C. The yield of nonvolatile product was 35.0 g. Based on the integration of the $^1$H NMR spectrum the conversion of hydroxyl groups is calculated to be 41%. Example 5 prepared above was dissolved in water at weight percent of 0.1%, and was tested for surface tension in accordance with Test Method 1. The results are in Table 3.

Example 6

Using the same procedure and workup as Example 5, polyethylene glycol (37.5 g, 0.025 mole, M$_n$=1500), NaH (0.07 g, 0.003 mole), and perfluoropropylvinyl ether (PPVE, 8.0 g 0.03 mole) were reacted to give 54.5 g product. Based on the integration of the $^1$H NMR spectrum the conversion of hydroxyl groups is calculated to be 37%. Example 6 prepared above was dissolved in water at weight percent of 0.1%, and was tested for surface tension in accordance with Test Method 1. The results are in Table 3.

Example 7

Using the same procedure and workup as Example 5, polyethylene glycol (50.0 g, 0.025 mole, M$_n$=2000), NaH (0.07 g, 0.003 mole), and perfluoropropylvinyl ether (PPVE, 8.0 g 0.03 mole) were reacted to give 40.6 g product. Based on the integration of the $^1$H NMR spectrum the conversion of hydroxyl groups is calculated to be 35%. Example 7 prepared above was dissolved in water at weight percent of 0.1%, and was tested for surface tension in accordance with Test Method 1. The results are in Table 3.

TABLE 3

| Example | Surface Tension nN/M |
| --- | --- |
| 1 | 22.9 |
| 2 | 22.9 |
| 3 | 24.2 |
| 4 | 20.9 |
| 5 | 21.5 |
| 6 | 27.4 |
| 7 | 34.4 |

The data in Table 3 shows that the examples of the present invention were effective to lower the surface tension of water from it's usual level of 72.8 mN/M at 20° C., at a low concentration of example of 0.1% by weight.

Testing of Examples

The aqueous solutions of mixtures of Examples 1 and 5, and Examples 2 and 5 were prepared, as indicated in Table 4, at a combined weight percent of 0.1% in water. These were tested for surface tension in accordance with Test Method 1. The results are in Table 4.

TABLE 4

| Example | Surface Tension nN/M |
| --- | --- |
| 0.05 wt % Example 1 + 0.05 wt % Example 5 | 19.8 |
| 0.05 wt % Example 2 + 0.05 wt % Example 5 | 19.9 |

The data in Table 4 shows that the mixture had a lower surface tension than the individual Examples as listed in Table 3.

Example 4 was mixed with a non-fluorinated surfactant, polyoxyethylene (2) oleyl ether (Brij 92) of structure: C$_{18}$H$_{35}$OCH$_2$CH$_2$OCH$_2$CH$_2$OH, which is available from Sigma-Aldrich, Milwaukee, Wis. The aqueous solution of the mixture of Example 4 and polyoxyethylene (2) oleyl ether (Brij 92) contained a combined weight percent of 0.1%, and the aqueous solution of polyoxyethylene (2) oleyl ether (Brij 92) contained 0.1% by weight. Each was tested for surface tension in accordance with Test Method 1. The results are in Table 5.

TABLE 5

| Surfactant Mixture | Surface Tension nN/M |
| --- | --- |
| 0.05 wt % Example 4 + 0.05 wt % Brij 92 | 21.3 |
| 0.1 wt % Brij 92 | 28.6 |

The data in Table 5 shows that the mixture containing Example 4 had a lower surface tension than the non-fluorinated surfactant.

Example 4 was added, at a level of 0.75% by weight, to a floor polish RHOPLEX 3829, Formulation N-29-1, available from Rohm and Haas Company, Philadelphia, Pa. The wetting and leveling ability of the floor finish, with and without Example 4, was tested in accordance with Test Method 2. The results are in Table 6.

TABLE 6

| | Leveling Effect in Floor Finish | |
| --- | --- | --- |
| Coating | 0.75 wt % Example 4 + floor polish | Control floor polish |
| 1$^{st}$ | 3 | 2 |
| 2$^{nd}$ | 5 | 2 |
| 3$^{rd}$ | 5 | 1 |
| 4$^{th}$ | 4.5 | 1 |
| 5$^{th}$ | 4 | 1 |

The data in Table 6 shows that the addition of Example 4 to the floor polish increased the leveling effect.

Example 4, in an amount shown in Table 7, was added to a semi-gloss acrylic latex paint from Vista Paint Corporation, Fullerton, Calif., having 2% by weight propylene glycol added. The blocking resistance of the paint, with and without Example 4, was tested on polyester panels in accordance with Test Method 3. The results are in Table 7.

TABLE 7

Blocking Resistance in Semi-Gloss Latex Paint

| Rating | Rating |
|---|---|
| 0.1 wt % Example 4 + latex paint | 6.0 |
| Control latex paint | 4.8 |

The data in Table 7 shows addition of Example 4 to the paint increased resistance to blocking.

Example 4, in an amount shown in Table 8, was added to a semi-gloss acrylic latex paint from Vista Paint Corporation, Fullerton, Calif., having 2% by weight propylene glycol added. The hiding power of the paint, with and without Example 4, was tested in accordance with Test Method 4. The results are in Table 8.

TABLE 8

Hiding Power in Semi-Gloss Latex Paint

| Rating | Contrast Ratio |
|---|---|
| 0.1 wt % Example 4 + Latex paint | 98% |
| Control latex paint | 93% |

The data in Table 8 shows the addition of Example 4 increased the hiding power of the paint.

Example 8

Polyethylene glycol (40.0 g, 0.10 mole, $M_n$=400), perfluoropropylvinyl ether (PPVE, 26.6 g 0.10 mole), and NaH (0.48 g, 0.02 mole) were reacted in 80 mL of anhydrous DMF (Aldrich Sure/Seal™) according to Example 4. The DMF was removed from the crude reaction mixture on a rotary evaporator at 60° C. The reaction mixture was added to 200 mL water and this mixture was extracted with three 100 mL portions of ether in a separatory funnel. The combined ether extracts were dried over $MgSO_4$, and concentrated in vacuo on a rotary evaporator to give an oil (41.8 g). $^1$H NMR ($\delta$, $d_6$-benzene) integration (see Example 4) showed conversion of hydroxyl groups consistent with this material being a mixture of $CF_3CF_2CF_2OCFHCF_2O[CH_2CH_2O]_x$ $CF_2CHFOCF_2CF_2CF_3$ (68 mole %) and $CF_3CF_2CF_2OCFHCF_2O[CH_2CH_2O]_xH$ (32 mole %). The aqueous layer was extracted with 150 mL of SOLKANE 365 mfc. The SOLKANE layer was separated and concentrated in vacuo on a rotary evaporator to give an oil (6.5 g). $^1$H NMR ($\delta$, $d_6$-benzene) integration (see Example 4) showed conversion of hydroxyl groups consistent with this material being a mixture of $CF_3CF_2CF_2OCFHCF_2O[CH_2CH_2O]_xH$ (74 mole %) and unreacted polyethylene glycol (26 mole %). Example 8 (SOLKANE extract) prepared above was dissolved in water at weight percent of 0.1%, 0.01%, 0.001% and was tested for surface tension in accordance with Test Method 1. The weights for preparing the solution were based on the estimate that this material is 82 wt % active ingredient (the $CF_3CF_2CF_2OCFHCF_2O[CH_2CH_2O]_xH$ fraction). The polyethylene glycol fraction is not expected to contribute to the reduction of surface tension. The results are in Table 9.

Example 9

Polyethylene glycol (60.0 g, 0.10 mole, $M_n$=600), perfluoropropylvinyl ether (PPVE, 39.9 g, 0.15 mole), and NaH (0.48 g, 0.02 mole) were reacted in 80 mL of anhydrous DMF (Aldrich Sure/Seal™) according to Example 4. The DMF was removed from the crude reaction mixture on a rotary evaporator at 60° C. The reaction mixture was added to 150 mL water and this mixture was extracted with two 150 mL portions of ether in a separatory funnel. The combined ether extracts were dried over $MgSO_4$, and concentrated in vacuo on a rotary evaporator to give an oil (61.8 g). $^1$H NMR showed essentially pure $CF_3CF_2CF_2OCFHCF_2O[CH_2CH_2O]_x$ $CF_2CHFOCF_2CF_2CF_3$. The aqueous layer was combined with 75 mL methanol (to control foaming), and concentrated in vacuo on a rotary evaporator to give an oil (15.5 g). $^1$H NMR ($\delta$, $d_6$-benzene) integration (see Example 4) showed conversion of hydroxyl groups consistent with this material being a mixture of $CF_3CF_2CF_2OCFHCF_2O[CH_2CH_2O]_xH$ (37 mole %) and unreacted polyethylene glycol (63 mole %). 7 g of this material was mixed with 20 mL of saturated aqueous NaCl solution and extracted three times with 10 mL SOLKANE 365 mfc. The cloudy SOLKANE layers were separated, combined, and concentrated in vacuo on a rotary evaporator to give an oil which was dissolved in minimal acetone and filtered to remove residual NaCl. The acetone was removed in vacuo to give an oil. $^1$H NMR ($\delta$, $d_6$-benzene) integration of peaks unique to the end groups: 3.63 (m, $OCH_2C\underline{H}_2OH$, relative area=1.05), 3.71 (t, $OCH_2C$ $\underline{H}_2OCF_2CFHOC_3F_7$, relative area=1.06), 5.55 (d, $^2J_{H-F}$=49 Hz, $OCH_2CH_2OCF_2CF\underline{H}OC_3F_7$, relative area=0.50) is consistent with this material being essentially pure $CF_3CF_2CF_2OCFHCF_2O[CH_2CH_2O]_x\underline{H}$. Example 9 (SOLKANE extract) prepared above was dissolved in water at weight percent of 0.1%, 0.01%, 0.001% and was tested for surface tension in accordance with Test Method 1. Results are in Table 9.

Example 10

Polyethylene glycol (100.0 g, 0.10 mole, $M_n$=1000), perfluoropropylvinyl ether (PPVE, 63.8 g, 0.24 mole), and NaH (0.48 g, 0.02 mole) were reacted in 80 mL of anhydrous DMF (Aldrich Sure/Seal™) according to Example 4. The DMF was removed from the crude reaction mixture on a rotary evaporator at 60° C. The reaction mixture was added to 200 mL water and this mixture was extracted with three 100 mL portions of ether in a separatory funnel. The combined ether extracts were dried over $MgSO_4$, and concentrated in vacuo on a rotary evaporator to give an oil (14.7 g). $^1$H NMR ($\delta$, $d_6$-benzene) showed an unexpected set of extra peaks in the $OCH_2CH_2OCF_2CF\underline{H}OC_3F_7$ region around 5.5 ppm. Three additional ether extractions (3×100 mL) were done on the aqueous layer. The combined second and third extractions yielded 20 g of oil and the fourth extraction yielded 7.9 g oil. $^1$H NMR ($\delta$, $d_6$-benzene) of the second, third and fourth extractions showed essentially pure $CF_3CF_2CF_2OCFHCF_2O$ $[CH_2CH_2O]_xCF_2CHFOCF_2CF_2CF_3$ with a single set of peaks for the $OCH_2CH_2OCF_2CF\underline{H}OC_3F_7$ and a barely detectable peak at 3.60 for the $OCH_2C\underline{H}_2OH$ end group. Example 10 (fourth ether extract) prepared above was dissolved in water at weight percent of 0.1%, 0.01%, 0.001% and was tested for surface tension in accordance with Test Method 1. Results are in Table 9.

TABLE 9

| Example | Surface Tension nN/M 0.1 wt % | Surface Tension nN/M 0.01 wt % | Surface Tension nN/M 0.001 wt % |
|---|---|---|---|
| 8 | 21.7 | 23.9 | 41.3 |
| 9 | 20.6 | 21.8 | 25.4 |
| 10 | 23.0 | 23.3 | 26.8 |

The data in Table 9 shows that Examples 8 to 10 were each effective in lowering the surface tension of water which is usually 72.8 mN/M at 20° C., at the low concentrations of 0.1% to 0.001% by weight.

Example 11

Tetraethylene glycol mono-methyl ether (14.56 g, 0.070 mole), perfluoropropyl vinyl ether (PPVE, 21.3 g, 0.08 mole), and NaH (0.17 g, 0.007 mole) were reacted in 100 mL of anhydrous DMF (Aldrich Sure/Seal™) according to Example 1. The crude reaction mixture was poured into 400 mL water and extracted with two portions of 300 mL diethyl ether. The combined ether extracts were dried over $MgSO_4$, and concentrated in vacuo on a rotary evaporator to give an oil (28 g). $^1$H NMR ($\delta$, $d_6$-acetone): 3.03 (s, $OCH_3$, 3.03H), 3.5, 3.6 3.75 (t, m, t, $CH_2$), 4.18 (t, $CH_2C\underline{H}_2OCH_3$, 1.98H), 6.61 (d, $^2J_{H\text{-}F}$=56 Hz, $OCH_2CH_2OCF_2CF\underline{H}OC_3F_7$). Based on the integration of the unique peaks due to the $CH_3$ and PPVE end groups, the conversion of hydroxyl group is quantitative. Example 11 prepared as above was dissolved in water at a weight percent of 0.1% and was tested for surface tension in accordance with Test Method 1. The results are in Table 10.

Example 12

Poly(ethylene glycol) mono-methyl ether (27.5 g, 0.05 mole, $M_n$=550), perfluoropropyl vinyl ether (PPVE, 15.96 g, 0.06 mole), and NaH (0.12 g, 0.005 mole) were reacted in 80 mL of anhydrous DMF (Aldrich Sure/Seal™) according to Example 1. The crude reaction mixture was poured into 500 mL water and extracted with two portions of 300 mL diethyl ether. Brine was added to improve the separation of the layers. The combined ether extracts were dried over $MgSO_4$, and concentrated in vacuo on a Kugelrohr to give an oil (30.7 g), a polyethylene glycol mono-methyl mono-fluorinated alkyl ether having the following structure $CF_3CF_2CF_2$—$OCFHCF_2O$—$[CH_2CH_2O]_x$—$CH_3$. $^1$H NMR ($\delta$, $d_6$-benzene): 3.11 (s, $OCH_3$, 3.1H), 3.27-3.44 (m, $CH_2$), 3.71 (t, $CH_2C\underline{H}_2OCH_3$, 1.9H), 5.53 (d, $^3J_{H\text{-}F}$=47 Hz, $OCH_2CH_2OCF_2CF\underline{H}OC_3F_7$, 0.94H). Based on the integration of the unique peaks due to the $CH_3$ and PPVE end groups, the conversion of hydroxyl group was quantitative. Example 12 prepared as above was dissolved in water at a weight percent of 0.1% and was tested for surface tension in accordance with Test Method 1. The results are in Table 10.

Example 13

Poly(ethylene glycol) mono-methyl ether (37.5 g, 0.05 mole, $M_n$=750), perfluoropropyl vinyl ether (PPVE, 15.96 g, 0.06 mole), and NaH (0.12 g, 0.005 mole) were reacted in 80 mL of anhydrous DMF (Aldrich Sure/Seal™) according to Example 1. Solvent was removed from the crude reaction mixture by high vacuum Kugelrohr distillation at 150° C. to give a solid (44.7 g), a polyethylene glycol mono-methyl mono-fluorinated alkyl ether having the following structure $CF_3CF_2CF_2$—$OCFHCF_2O$—$[CH_2CH_2O]_x$—$CH_3$. $^1$H NMR ($\delta$, $d_6$-benzene): 2.86 (bs, $CH_2CH_2O\underline{H}$), 3.12 (s, $OCH_3$, 3H), 3.28-3.46 (m, $CH_2$), 3.62 (t, $CH_2C\underline{H}_2OH$), 3.72 (t, $CH_2C\underline{H}_2OCH_3$, 0.834H), 5.57 (d, $^2J_{H\text{-}F}$=54 Hz, $OCH_2CH_2OCF_2CF\underline{H}OC_3F_7$, 0.366H). Based on the integration of the unique peaks due to the $CH_3$ and PPVE end groups, the conversion of hydroxyl groups was 40%. Example 13 prepared as above was dissolved in water at a weight percent of 0.1% and was tested for surface tension in accordance with Test Method 1. The results are in Table 10.

Example 14

Poly(ethylene glycol) mono-methyl ether (50 g, 0.025 mole, $M_n$=2000), perfluoropropyl vinyl ether (PPVE, 8.0 g, 0.03 mole), and NaH (0.06 g, 0.0025 mole) were reacted in 80 mL of anhydrous DMF (Aldrich Sure/Seal™) according to Example 1. The reaction mixture was poured into 500 mL water and the mixture was extracted with two 300 mL portions of $CHCl_3$. Solvent was removed from the extracts by high vacuum Kugelrohr distillation at 140° C. to give a white solid (54.3 g), a polyethylene glycol mono-methyl mono-fluorinated alkyl ether having the following structure $CF_3CF_2CF_2$—$OCFHCF_2O$—$[CH_2CH_2O]_x$—$CH_3$. $^1$H NMR ($\delta$, $d_6$-acetone): Based on the integration of the unique peaks due to the $CH_3$ and PPVE end groups (Example 11), the conversion of hydroxyl group was 72%. Example 14 prepared as above was dissolved in water at a weight percent of 0.1% and was tested for surface tension in accordance with Test Method 1. The results are in Table 10.

TABLE 10

| Example | Surface Tension nN/M |
|---|---|
| 11 | 22.3 |
| 12 | 22.2 |
| 13 | 21.7 |
| 14 | 34.7 |

The data in Table 10 shows that Examples 11 to 14 were each effective in lowering the surface tension of water which is usually 72.8 mN/M at 20° C.

What is claimed is:

1. A compound comprising Formula I, or a mixture thereof,

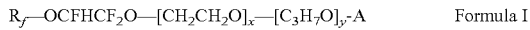

$R_f$—$OCFHCF_2O$—$[CH_2CH_2O]_x$—$[C_3H_7O]_y$-A     Formula I wherein
 $R_f$ is  $C_nF_{2n+1}$,
 n is 1 to about 6,
 x is a mixture of positive integers and is 4 or greater,
 y is 0 to about 4, provided that the ratio of y to x is equal to or less than 0.25,
 A is $R_fOCHFCF_2$ or $C_mH_{2m+1}$, and
 m is 1 to about 24.

2. The compound of claim 1 wherein n is 1 to about 4.

3. The compound of claim 1 wherein x is a mixture of positive integers of from about 9 to about 25.

4. The compound of claim 1 wherein $R_f$ is $C_3F_7$, x is from about 12 to about 18, y is 0, and A is $R_fOCHFCF_2$ or $C_mH_{2m+1}$ wherein m is 1.

5. The compound of claim 1, or a mixture thereof, having a surface tension of less than about 25 mN/M at a concentration of 0.1% by weight in water.

6. The compound of claim 1, or a mixture thereof, having a surface tension of less than about 20 mN/M at a concentration of 0.1% by weight in water.

7. The compound of claim 1, or a mixture thereof, further comprising a non-fluorinated surfactant or a fluorinated surfactant.

8. A method of altering the surface behavior of a liquid comprising adding to the liquid a compound comprising Formula I, or a mixture thereof,

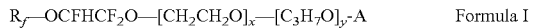

$$R_f\text{—OCFHCF}_2\text{O—[CH}_2\text{CH}_2\text{O]}_x\text{—[C}_3\text{H}_7\text{O]}_y\text{-A} \qquad \text{Formula I}$$

wherein
$R_f$ is $C_nF_{2n+1}$,
n is 1 to about 6,
x is a mixture of positive integers and is 4 or greater.
y is 0 to about 4, provided that the ratio of y to x is equal to or less than 0.25,
A is $R_fOCHFCF_2$ or $C_mH_{2m+1}$, and
m is 1 to about 24,
or a mixture thereof.

9. The method of claim 8 wherein the altering of surface behavior is lowering the surface tension.

10. The method of claim 8 wherein the surface behavior is selected from the group consisting of wetting, penetration, spreading, leveling, flowing, emulsifying, dispersing, repelling, releasing, lubricating, etching, bonding, and stabilizing.

11. The method of claim 10 wherein the liquid is a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor finish, or bonding agent.

12. The method of claim 10 wherein the liquid is a coating composition.

13. The method of claim 12 wherein the surface behavior is resistance to blocking in the coating composition after drying.

14. The method of claim 12 wherein the surface behavior is wetting and leveling during application of the coating composition to a surface.

15. The method of claim 10 wherein the liquid is a floor finish.

16. The method of claim 15 wherein the surface behavior is leveling.

\* \* \* \* \*